United States Patent [19]
Uchida et al.

[11] Patent Number: 6,078,829
[45] Date of Patent: Jun. 20, 2000

[54] MEASURING APPARATUS FOR BIOLOGICAL INFORMATION

[75] Inventors: Shinji Uchida, Neyagawa; Hiroshi Atsuta, Katano; Kiyoko Ooshima, Shijonawate, all of Japan

[73] Assignee: Matsuhita Electric Industrial Co., Ltd., Osaka, Japan

[21] Appl. No.: 09/212,397

[22] Filed: Dec. 16, 1998

[30] Foreign Application Priority Data

Dec. 14, 1997 [JP] Japan .................................. 9-348174

[51] Int. Cl.$^7$ ........................................................ A61B 5/00
[52] U.S. Cl. ............................................ 600/310; 600/340
[58] Field of Search .................................. 600/310, 322, 600/323, 340, 344

[56] References Cited

U.S. PATENT DOCUMENTS

| | | |
|---|---|---|
| 4,653,498 | 3/1987 | New, Jr. et al. ..................... 600/323 |
| 5,213,099 | 5/1993 | Tripp, Jr. . |
| 5,372,134 | 12/1994 | Richardson . |
| 5,673,692 | 10/1997 | Schulze et al. . |

FOREIGN PATENT DOCUMENTS

| | | |
|---|---|---|
| 0770349 | 9/1996 | European Pat. Off. . |
| 08066378 | 12/1996 | Japan . |
| 2284060 | 5/1995 | United Kingdom . |

*Primary Examiner*—Eric F. Winakur
*Attorney, Agent, or Firm*—McDermott, Will & Emery

[57] ABSTRACT

The present invention provides a measuring apparatus for biological information which permits accurate determination for biological information without causing the subject much discomfort. The measuring apparatus for biological information of the present invention uses an ear receiver-shaped sensor element which is placed and held on the perimeter of the subject's external auditory meatus opening with the light emitter and the light receiver brought into contact with the subject. The light receiver detects the light projected to and passed through the subject. The apparatus is also provided with a signal processor which performs calculation for biological information of the subject on the basis of the intensity of light detected by the light receiver.

11 Claims, 5 Drawing Sheets

MEASURING APPARATUS FOR BIOLOGICAL INFORMATION

BACKGROUND OF THE INVENTION

The present invention relates to a measuring apparatus for biological information to carry out noninvasive determination of biological information such as pulse rate and blood sugar level.

A number of measuring apparatuses for biological information have been proposed. For example, Japanese Laid-Open Patent Publication No. Hei 8-66378 has disclosed a pulsimeter for measuring a pulse rate on the basis of a change in intensity of light passed through an earlobe. A measuring terminal disclosed in the publication is outlined in FIG. 5.

Figure 5:
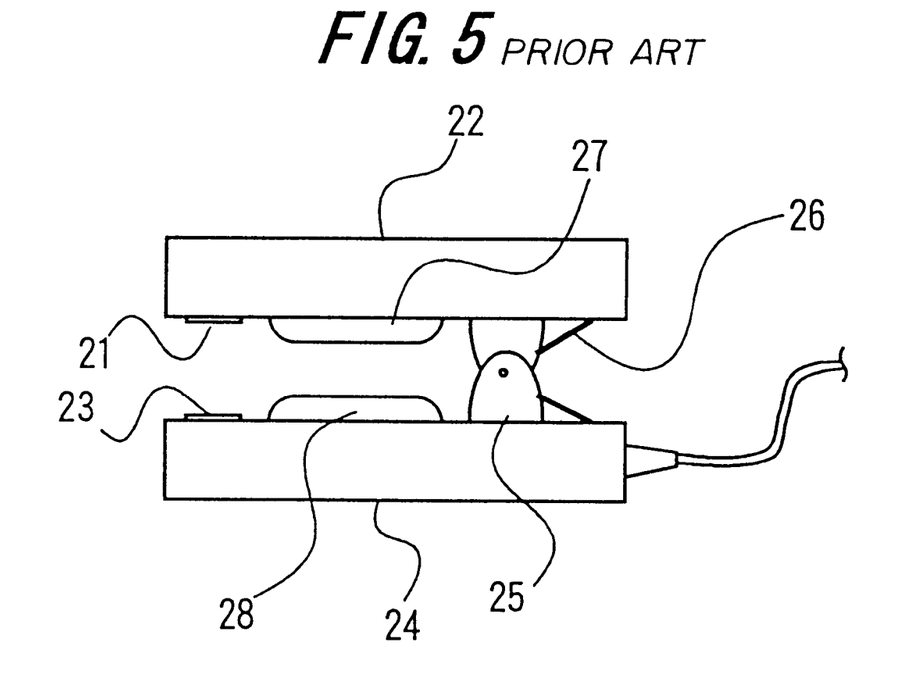
FIG. 5 is a side view of the measuring terminal of the prior art pulsimeter.

As shown, the measuring terminal includes a pair of gripping pieces 22 and 24 which are jointed by a jointing elements 25 and pressed against each other by a spring 26. The gripping pieces 22 and 24 are provided with contact pads 27 and 28, respectively. Further, a light emitting element 21 and a light receiving element 23 are arranged on the gripping piece 22 and 24, respectively, so as to face each other. In taking a measurement, the measuring terminal of the pulsimeter is placed on the earlobe with the two gripping pieces 22 and 24 holding the earlobe therebetween, and a light is emitted from the light emitting element 21. The light receiving element 23 detects the light projected by the light emitting element 21 and passed through the earlobe.

A blood flow is not uniform but pulsates. Besides, a light transmittance through blood is lower than that through other substances forming a living body such as, for example, the skin. Therefore, an intensity of the light passed through the earlobe changes in rhythm with the pulse. The prior art pulsimeter calculates the pulse rate on the basis of the change in the intensity of light passed through the earlobe. Measurement of the pulse rate can be taken on other parts than the earlobe. For accurate determination, the light emitting element 21 and the light receiving element 23 are located apart from the contact pads 27 and 28, respectively.

However, such a pulsimeter presents the following problems.

The measuring terminal of the pulsimeter is pressed against the earlobe and left hanging therefrom during the measurement. When measurement is taken with a moving subject as in measurement of the pulse rate of a person in motion, the measuring terminal swings, thereby causing an increase in load on the earlobe hanging the measuring terminal. That makes it difficult to take an accurate measurement, and also causes a feeling of physical disorder and discomfort for the subject. A long measurement session, in particular, could turn such feeling of physical disorder and discomfort to mental pain.

Thus, it is an object of the present invention to provide a measuring apparatus for taking a biological information which can solve those problems and permits accurate measurements for taking biological information without causing the subject much discomfort or the like.

BRIEF SUMMARY OF THE INVENTION

According to the present invention, an ear receiver-shaped sensor element for placing and being held on the perimeter of the subject's external auditory meatus opening is employed. The sensor element is provided with a light emitter and a light receiver at an area where the sensor element comes into contact with the subject. Of the light projected by the light emitter, the component which reflected from the subject or transmitted therethrough is measured to obtain biological information.

The measuring apparatus for biological information of the present invention is provided with a sensor element for placing and being held on the perimeter of the subject's external auditory meatus opening. The light emitter and the light receiver are so arranged as to contact the subject. For example, the end face of the light emitter and the end face of the light receiver are arranged on the same plane of the same sensor element. The light receiver of such sensor element detects the light reflected from the subject after slightly penetrating into the subject, out of the light projected by the light emitter. On the basis of the intensity of light detected by the light receiver, calculation is made for taking the biological information.

A small-sized light emitting diode (LED) element may be employed as a light emitter, for example.

A photodiode of Si or a pyroelectric microsensor may be employed as a photodetector for the light receiver, for example. By using either of those, a small-sized and light-weight photodetector can be obtained. It is reported in an article "Microsensor" by Takayama et al. in a Japanese technical monthly magazine "Monthly New Ceramics", Vol. 7, No. 12 (published on December 1994), for example, that a microsensor with the one side not longer than 1 mm can be produced.

Thus, the sensor element can be miniaturized by utilizing the known technology. That makes it possible to fabricate an ear receiver-shaped sensor element of the so-called "inner ear-type" which can be fitted in the space formed by a tragus at the perimeter of an external auditory meatus opening, an antihelix and a concha of auricle.

Those small light emitter and photodetector may be either directly imbedded in the sensor element. Those may also be provided outside the sensor element and connected to the sensor element via an optical fiber so that the end of the optical fiber may be put on the subject.

A pair of the sensor elements may also be put on both ears just like the headphone. In such cases, a large-sized sensor element which is shaped into the so-called closed-type or the open air-type headphone can be employed instead of the inner ear-type ones, if the light emitter and the light receiver can be arranged so as to have close contact with the perimeter of the subject's external auditory meatus openings by using a headband or the like. A large sensor element, especially, is easy to handle in use, because the sensor element and the signal processor can be integrated. The aforesaid sensor element may be substituted by a pair of similarly-shaped elements, one having the light emitter only and the other having the light receiver only. The idea is that the light projected by the light emitter in one ear is detected by the element held in the other ear. The intensity of light passed through the head of the subject is measured and used for the calculation for taking biological information of the subject. Of such sensor elements having various arrangements, the one with a headband is preferred, because stable detection of light by the light receiver is ensured.

The biological information thus obtained is then reported to the subject in acoustic signals from an acoustic oscillator, for example. The results are also shown on a display such as a liquid crystal display.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

The measuring apparatus for biological information of the present invention includes a sensor element and a signal processor. The sensor element includes a light emitter which projects a light to the subject and a light receiver which receives the light reflected from the subject after penetrating in the subject. The signal processor performs calculation for taking biological information of the subject on the basis of the intensity of light detected by the light receiver. The sensor element is so formed that the light emitter and the light receiver are placed and held on the perimeter of the subject's external auditory meatus opening.

In the use of the measuring apparatus for biological information of the present invention, a light is projected to the subject and an intensity of the reflected light is measured to obtain biological information such as concentrations of specific substances and a pulse rate. Part of the light projected on the subject penetrates and reflected therefrom. Of the light penetrating the living body, certain wavelength components are absorbed by light-absorbing substances in the light path such as glucose and cholesterol in the blood. Therefore, information of a concentration of the light-absorbing substance can also be obtained by projecting a light including the wavelength components which well penetrate into the living body and are easily absorbed by the light-absorbing substance, then by detecting the reflected light for analyzing.

When the measuring apparatus for biological information of the present invention is used as pulsimeter, the reflected light is measured continuously. While most of the compositions in the living body are stationary, the blood flow pulsates. The intensity of the reflected light changes in rhythm with the pulse rate. Therefore, the pulse rate can be measured by observing the change in the reflected light intensity.

In the present invention, the intensity of reflected light is measured on the perimeter of the external auditory meatus opening, in particular. There, the sensor element can be held securely, and the light emitter and the light receiver are hardly loosen from the subject even when the subject is in motion. Thus, accurate determination is ensured. It is also noted that the light emitter and the light receiver can be so miniaturized by conventional technology as not to weigh on the subject when these are put on the ear.

Another measuring apparatus for biological information of the present invention includes a first sensor element which has a light emitter for projecting a light to a subject, a second sensor element for detecting the light passed through the subject out of the light projected by the light emmiter, and a signal processor for calculating biological information of the subject on the basis of the intensity of the light detected by the light receiver. The first and second sensor elements are so formed that the light emitter and the light receiver are brought into contact with, and held on the perimeters of the subject's external auditory meatus openings.

In that measuring apparatus for biological information, the use of a plurality of light receivers increases the reliability of determination. For example, even if one of the light receivers comes off, normal measurement can be continued with the other light receiver put in position. Furthermore, a plurality of light rays passed through different paths can be detected. An abnormal measurement could be eliminated with a high degree of accuracy achieved.

A preferred embodiment of the measuring apparatus for biological information additionally includes an acoustic oscillator, that is, a speaker. If, for example, an acoustic oscillator is built in the sensor element, the sensor element can function as an ear receiver. Furthermore, biological information obtained from a measurement and also the start or end of the measurement can be notified to the subject from the acoustic oscillator in the form of acoustic signal. Needless to say, the acoustic oscillator can be mounted outside the sensor element.

A message to the subject of biological information, the start or end of the measurement can be shown on the display, too. For example, a liquid crystal display can be placed on the wiring connecting the sensor element and the signal processor so that the subject can look at the display handily. Also, a small and light-weight liquid crystal display would not be a burden to the subject.

As set forth above, the measuring apparatus for biological information of the present invention permits measurement for a variety of biological information on a stable basis. For application as pulsimeter, the signal processor can be substantially reduced in size and simplified.

Now, a pulsimeter as an example of the measuring apparatus for biological information of the present invention will be described.

Figure 1:
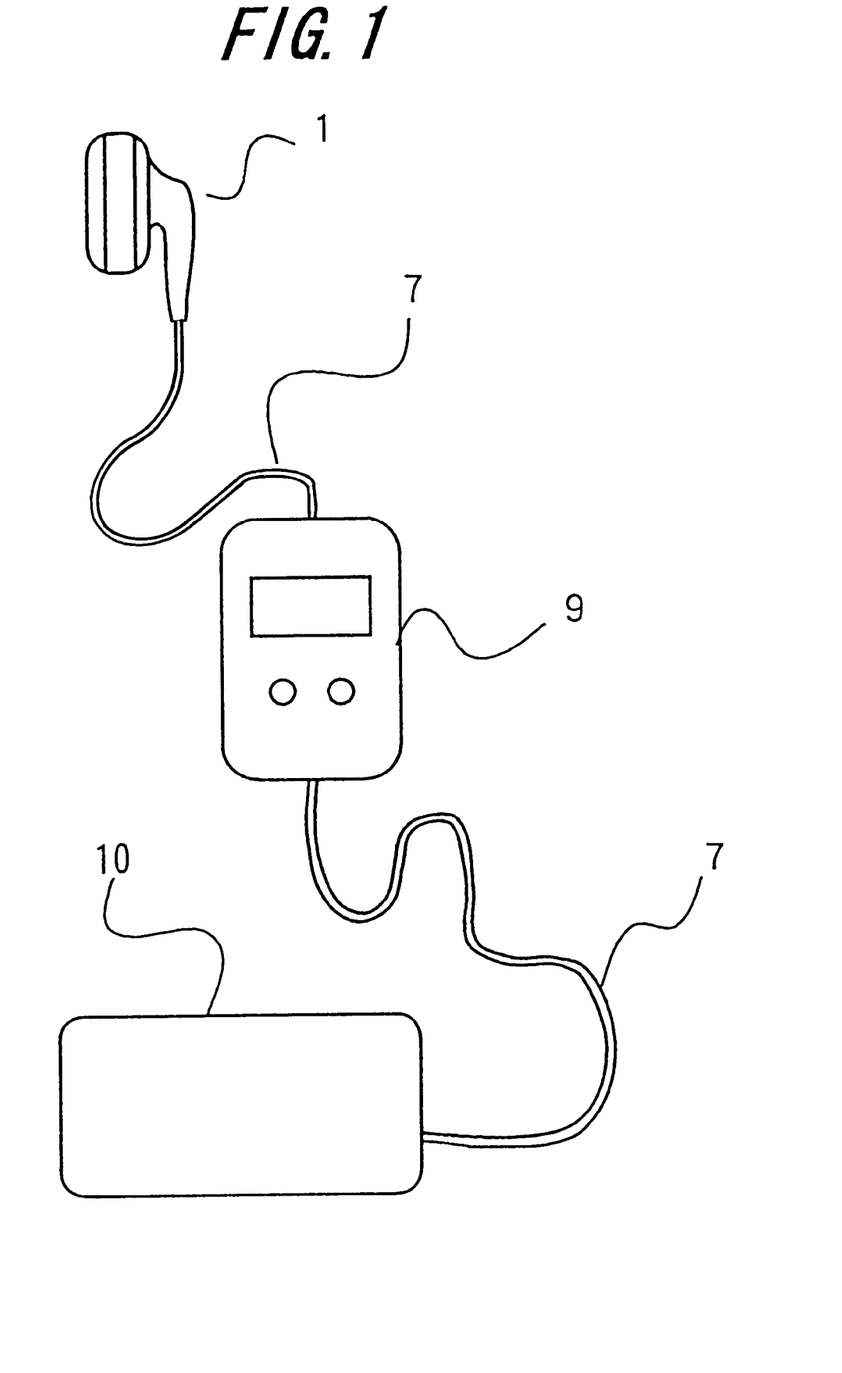
FIG. 1 is a schematic view of a measuring apparatus for biological information in an embodiment of the present invention.
Figure 3:
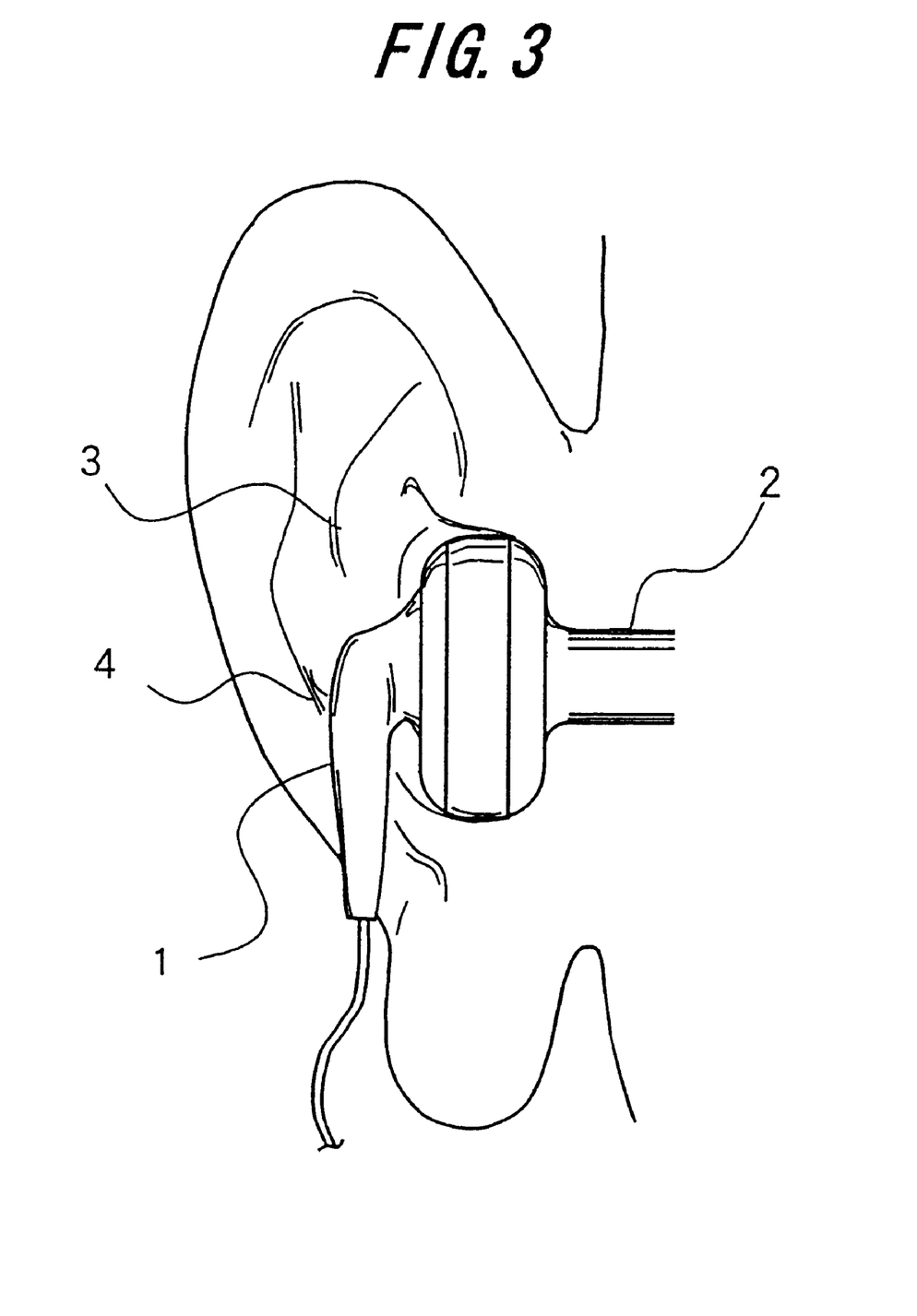
FIG. 3 shows the same sensor element worn in the ear.

FIG. 1 shows a measuring apparatus for biological information with an ear receiver-shaped sensor element 1 of the so-called inner ear type. The sensor element 1 is fitted and held in a space surrounded by a tragus (a projection at the front of an external ear, not shown) at the opening of the subject's external auditory meatus 2, an antihelix 3 and a concha of auricle 4 just as the usual ear receiver as shown in FIG. 3.

A light emitter 5 and a light receiver 6 are so arranged on the side of the sensor element 1 facing the opening of the external auditory meatus 2 as to come in close contact with the subject. The light emitter 5 projects a light to the subject. For use as pulsimeter, an LED element capable of projecting a light with a wavelength of 960 nm, for example, is used as the light emitter 5.

The light receiver 6 detects a component of the light projected by the light emitter 5 and reflected from the subject. An example of the light receiver 6 is a pyroelectric sensor.

The measurement can be done using a sensor element with sole light receiver. But considering the possibility of the light receiver coming off, it is desirable to use a sensor element with a plurality of light receivers. Provision of a plurality of light receivers brings information on the light rays which passed through different paths in the subject, which increases a precision of measurement. In that case, it is desired that the light receivers are arranged on a circle concentric with the light emitter.

Figure 4:
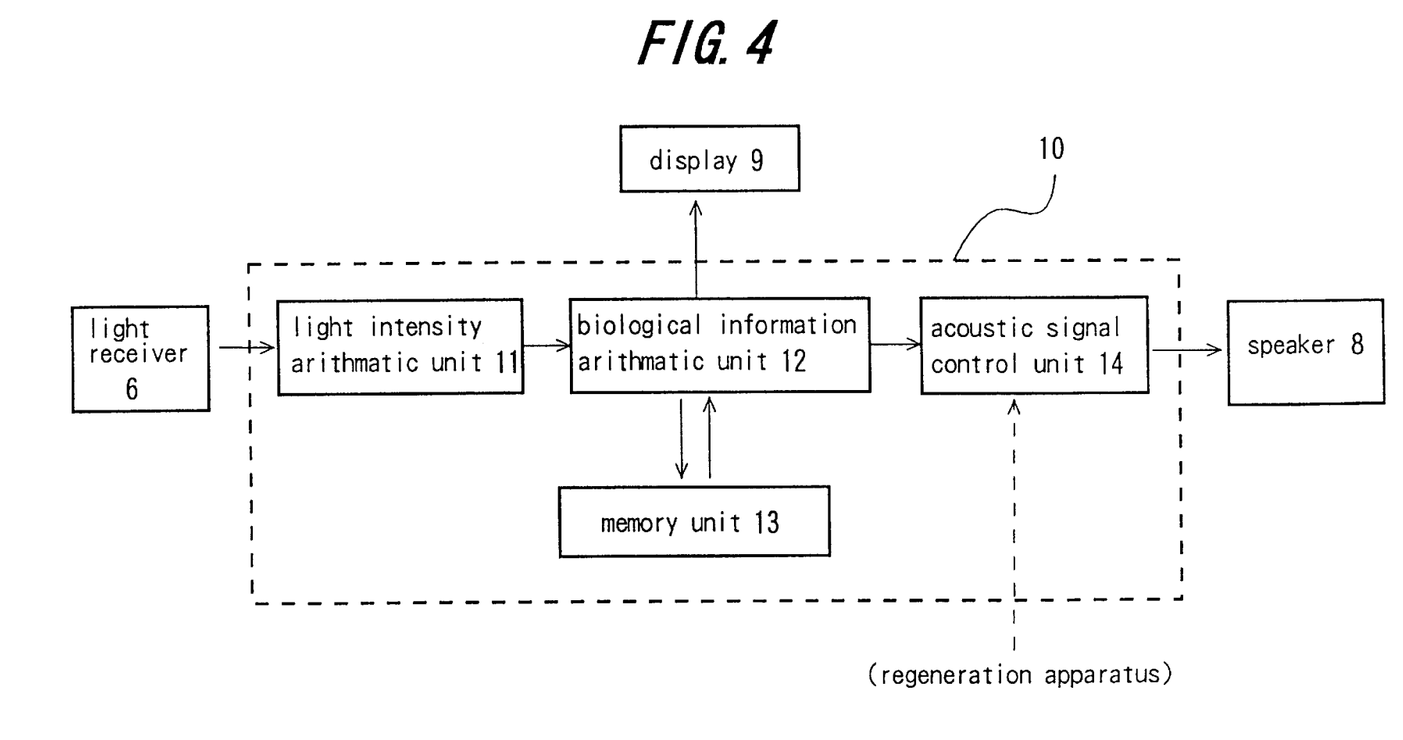
FIG. 4 is a block diagram showing a configuration of a signal processor of the same measuring apparatus for biological information.

The light receiver 6 outputs to a signal processor 10 signals corresponding to the intensity of the light detected. The signal processor 10 is provided with a light intensity arithmetic unit 11, a biological information arithmetic unit 12, a memory unit 13 and an acoustic signal control unit 14 as shown in FIG. 4.

The output signals from the light receiver 6 are first inputted to the light intensity arithmetic unit 11. The light intensity arithmetic unit 11 monitors the change in intensity of the inputted signals, recognizes the start and end of measurement, and also watches for abnormalities in the measurement. The biological information arithmetic unit 12 calculates a pulse rate of the subject on the basis of the signals from the light intensity arithmetic unit 11. The pulse rate obtained is shown on a display 9. The display 9 is located on the wiring connecting the sensor element 1 with the signal processor 10 as in FIG. 1, for example. Especially in a case the display 9 is a small-sized light-weight liquid crystal display, a hanging wiring 7 will not be a burden to the subject. Also, the subject can see the display without difficulty even in motion. The display 9 may additionally include a switch to start or stop the measurement. The biological information obtained is stored in a magnetic recording medium, a semiconductor memory or the like.

Figure 2:
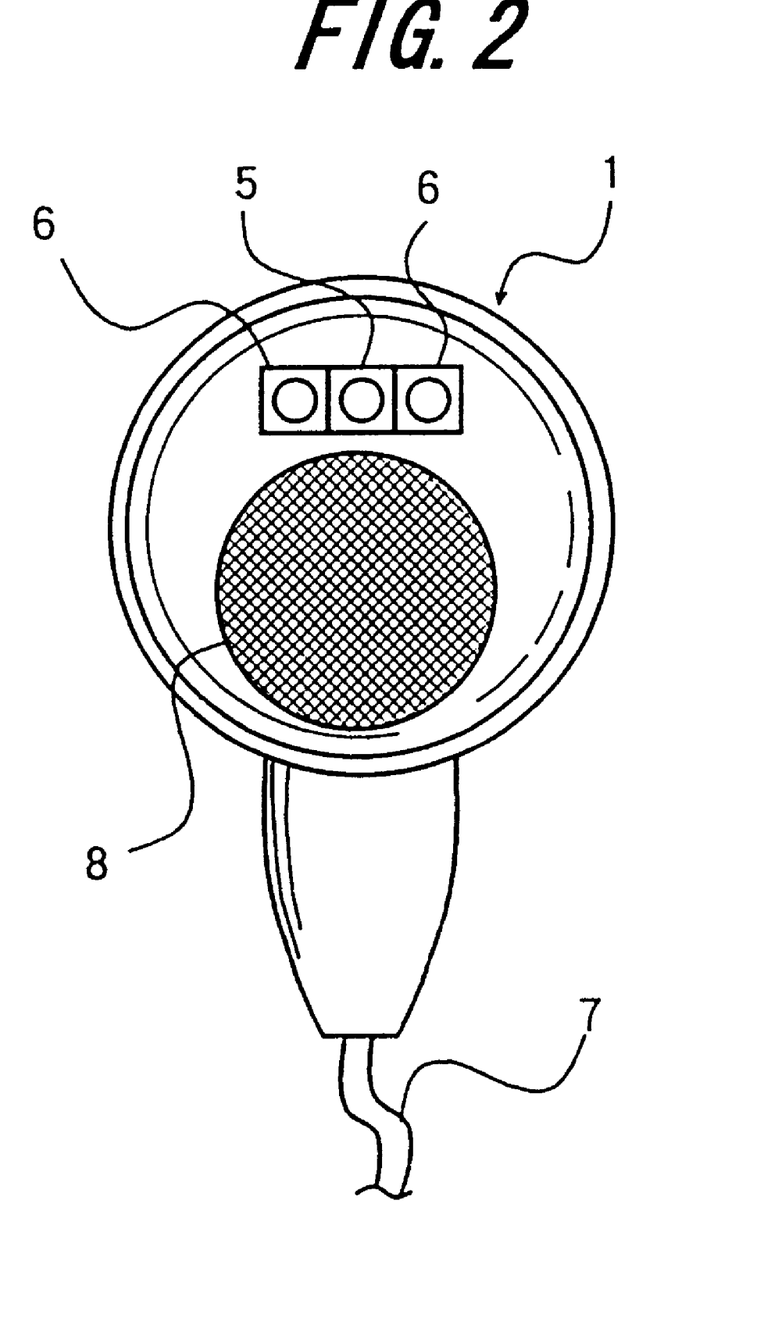
FIG. 2 is a plan view of a sensor element used in the same measuring apparatus for biological information.

In the present embodiment, the measuring apparatus for biological information is provided with a speaker 8 as an acoustic oscillator on the side facing the external auditory meatus as shown in FIG. 2. The acoustic signal control unit 14 in the signal processor 10 converts into acoustic signals the biological information worked out by the biological information arithmetic unit 12, and forwards those signals to the speaker 8. Thus, the biological information obtained is reported to the subject in the form of acoustic signals. For example, the acoustic signal control unit 14 makes the speaker 8 send the acoustic signals such as a prerecorded message in an artificial human voice, if the pulse rate calculated by the signal processor 10 exceeds a specific level.

By providing a sensor element with the speaker as above, the sensor element can be made to serve as an ear receiver, too. That is, when the measurement is not done, music or the like can be played to the speaker from a reproduction medium such as a magnetic tape and compact disc. Even in measurement, while playing music or the like using the reproduction medium, the acoustic signals for biological information or other messages such as the start or the end of the measurement may be superimposed on the much sound or may be sounded out with the sound interrupted.

For determination of a glucose concentration or a fatty acid concentration, that is, the cholesterol level in blood, a halogen lamp which emits light rays with a wavelength ranging from 400 to 2,200 nm may be employed as the light emitter 5. For this measurement, the reflected light is introduced to a band pass filter which allows only a specific wavelength component for which the substance exhibits a high absorption coefficient to pass therethrough. For determination of the glucose concentration, only components with a wavelength of 1,600 nm or around are allowed to pass therethrough. For determination of the fatty acid concentration, only components with a wavelength of 960 nm or around are allowed to pass therethrough. The transmitted light is detected by a photodetector made with Si, InGaAs, Ge, etc. Analysis of the intensity of light detected by the photodetector produces the object biological information.

It is also possible to obtain biological information on a plurality of indicators at a time by splitting the reflected light into specific bands using a spectroscope and by picking up specific wavelength components using different band filters.

To embed all those in a sensor element would increase the size of the sensor element. Also, the use of a halogen lamp presents such problems as the size, intensity and heating. As a solution to the problems, a light source and a spectroscope may be installed outside the sensor element and connected with the light emitter and the light receiver on the sensor element via an optical fiber, respectively.

Thus, the present invention provides a measuring apparatus for biological information which permits accurate determination for taking biological information without causing the subject much discomfort.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications ias fall within the true spirit and scope of the invention.

What is claimed is:

1. A measuring apparatus for biological information which comprises: a sensor element having a light emitter for projecting light to a subject and a light receiver for receiving a light reflected from said subject out of the light projected by said light emitter; a signal processor which performs calculation for taking biological information of said subject on the basis of the intensity of light detected by said light receiver; and an acoustic oscillator, wherein said sensor element has a shape which allows each of said light emitter and said light receiver to be brought into contact with and held on the perimeter of an external auditory meatus opening of said subject, and said acoustic oscillator is provided on a side of said sensor element, said side facing the external auditory meatus.

2. The apparatus for measuring biological information in accordance with claim 1, wherein said sensor element has a plurality of light receivers.

3. The apparatus for measuring biological information in accordance with claim 1, wherein said acoustic oscillator is provided within said sensor element.

4. The apparatus for measuring biological information in accordance with claim 1, wherein said acoustic oscillator outputs the biological information as acoustic signals.

5. The apparatus for measuring biological information in accordance with claim 1, further comprising a display for displaying the biological information.

6. An apparatus for measuring biological information which comprises: a first sensor element having a light emitter for projecting light to a subject; a second sensor element having a light receiver for receiving light passed through said subject out of the light projected by said light emitter; and a signal processor which calculates biological information of said subject on the basis of the intensity of light detected by said light receiver, wherein each of said first and second sensor elements has a shape which allows said light emitter and said light receiver to be brought into contact with and held on the perimeter of an external auditory meatus opening of said subject.

7. The apparatus for measuring biological information in accordance with claim 6, wherein said second sensor element has a plurality of light receivers.

8. The apparatus for measuring biological information in accordance with claim 6, further comprising an acoustic oscillator.

9. The apparatus for measuring biological information in accordance with claim 8, wherein said acoustic oscillator is provided adjacent said first sensor element.

10. The apparatus for measuring biological information in accordance with claim 8, wherein said acoustic oscillator outputs the biological information as acoustic signals.

11. The apparatus for measuring biological information in accordance with claim 6, further comprising a display for displaying the biological information.

* * * * *

UNITED STATES PATENT AND TRADEMARK OFFICE
CERTIFICATE OF CORRECTION

PATENT NO.   : 6,078,829
DATED        : June 20, 2000
INVENTOR(S)  : Shinji Uchida, et al.

It is certified that error appears in the above-identified patent and that said Letters Patent is hereby corrected as shown below:

On the Title page:

Section [30], under Foreign Application Priority Data, change the filing date from "December 14, 1997" to --December 17, 1997--.

Section [73], change the Assignee's name from "Matsuhita Electric Industrial Co., Ltd. "to --Matsushita Electric Industrial Co., Ltd.--.

Signed and Sealed this

Twelfth Day of June, 2001

*Attest:*

*Attesting Officer*

NICHOLAS P. GODICI
*Acting Director of the United States Patent and Trademark Office*